(12) United States Patent
Kitamura et al.

(10) Patent No.: US 7,759,316 B2
(45) Date of Patent: Jul. 20, 2010

(54) BIODEGRADABLE ARTICLES OBTAINED FROM ENZYMATICALLY SYNTHESIZED AMYLOSE

(75) Inventors: Shinichi Kitamura, Kyoto (JP); Nobuo Shiraishi, Kyoto (JP); Mariko Yoshioka, Kyoto (JP); Kenichi Kudo, Nara (JP); Shigetaka Okada, Osaka (JP); Takeshi Takaha, Osaka (JP); Kazutoshi Fujii, Osaka (JP); Yoshinobu Terada, Osaka (JP)

(73) Assignees: Ezaki Glico Co., Ltd., Osaka (JP); Sanwa Kosan Kabushiki Kaisha, Nara (JP)

( * ) Notice: Subject to any disclaimer, the term of this patent is extended or adjusted under 35 U.S.C. 154(b) by 1882 days.

(21) Appl. No.: 10/333,267

(22) PCT Filed: Jul. 17, 2001

(86) PCT No.: PCT/JP01/06147

§ 371 (c)(1),
(2), (4) Date: Jan. 17, 2003

(87) PCT Pub. No.: WO02/06507

PCT Pub. Date: Jan. 24, 2002

(65) Prior Publication Data

US 2004/0009218 A1 Jan. 15, 2004

(30) Foreign Application Priority Data

Jul. 17, 2000 (JP) .............................. 2000-216335

(51) Int. Cl.
*A61K 9/48* (2006.01)
(52) U.S. Cl. .......................... 514/23; 424/400; 424/443; 424/488
(58) Field of Classification Search ........................ None
See application file for complete search history.

(56) References Cited

U.S. PATENT DOCUMENTS 3,879,212 A * 4/1975 Yoshida et al. ........... 106/162.1
5,405,449 A * 4/1995 Gotlieb et al. ................ 127/71

(Continued)

FOREIGN PATENT DOCUMENTS

EP 376201 7/1990

(Continued)

OTHER PUBLICATIONS

Sigma Catalog, 1992 Edition Product Number A 0512.*

(Continued)

*Primary Examiner*—Robert A Wax
*Assistant Examiner*—Melissa S Mercier
(74) *Attorney, Agent, or Firm*—Wenderoth, Lind & Ponack, L.L.P.

(57) ABSTRACT

The present invention provides a biodegradable article formed from enzyme-synthesized amylose using phosphorylase, wherein the enzyme-synthesized amylose is composed of glucose monomers exclusively bonded by α-1,4-glucosidic likage and has a weight average molecular weight of not less than 100 kDa, preferable not less than 600 kDa. The enzyme-synthesized amylose employed in the present invention has a molecular weight distribution (Mw/Mn) of not more than 1.25 and can be chemically modified if desired.

The biodegradable article of the present invention can be produced by (a) the enzyme-synthesized amylose and/or its modified one, or a combination of the amylose (a) and another polymer material (b).

12 Claims, 1 Drawing Sheet

U.S. PATENT DOCUMENTS 5,681,123 A * 10/1997 Yamaguchi ................. 400/586
5,686,132 A * 11/1997 Takaha et al. ............... 426/658
5,703,160 A * 12/1997 Dehennau et al. ........ 525/54.24

FOREIGN PATENT DOCUMENTS

| EP | 0 590 736 | 4/1994 |
|---|---|---|
| EP | 0 608 040 | 7/1994 |
| JP | 4-46901 | 2/1992 |
| JP | 7-289278 | 11/1995 |
| WO | 90/13576 | 11/1990 |

OTHER PUBLICATIONS

Sigma Chemical Company Catalog: 1992 edition; product a0512.*
Sigma Chemical Catalog; 1992 edition, Amylose.*
G.M. Whitesides et al., "Th enzymicutilization of sucrose in the synthesis of amylose and derivatives of amylose, using phosphorylase", Carbohydrate Research, 157, pp. c4 to c7, Dec. 1986.
Pierre Monsan et al., "Amylosucrase from *Neisseria polysaccharea*: novel catalytic properties", FEBS Letters, 471, pp. 219 to 223, Apr. 2000.

* cited by examiner

Fig. 1

BIODEGRADABLE ARTICLES OBTAINED FROM ENZYMATICALLY SYNTHESIZED AMYLOSE

TECHNICAL FIELD

The present invention relates to a biodegradable article, particularly to a biodegradable article formed from an amylose that is synthesized using phosphorylase

DEFINITION OF TERMS

The term "article" is employed with a broad concept where it not only includes object having some shape usually considered for the term "article" but also includes object without shape. It, however, excludes food, food additive or a capsule that contains content therein. More concretely, the term "article" includes an article usually formed from synthetic polymer, such as (i) molded article including film, sheet, containers and wrappage, (ii) paint or adhesive, and (iii) pharmaceuticals or agricultural chemicals or fertilizer.

Although the term "capsule" generally means a container encapsulating medicine that is difficult to orally take or the like, it means herein a container itself that does not contain any content. The term "capsule agent" used herein means the usual "capsule" that contains some content therein. Although the term "capsule" may very broadly include material merely covered with resin or like or crushed mixture of resin and another material, the "capsule" used herein does not use such broad meaning.

BACKGROUND ART

Synthetic polymer that is easily made from petroleum as raw material and has been produced with very large amount on the earth causes social problem for disposal of waste polymer, because it emits poisonous gas when it burns and does not degrade in natural surroundings. Additionally, it is pointed out that petroleum-made plastics, such as polystyrene or polycarbonate, contain environmental hormone which may injure living of the human beings. Additionally plastics often contain some oligomer, but it has been warned that the oligomer may harm the human bodies.

It is also noted to replace petroleum plastics with agricultural product, especially starch material, in view of energy and resource strategy after exhaustion of petroleum resource and zero-emission system of carbon dioxide.

Thus another polymeric material obtained from starch or wood has been developed in lieu of such polymeric materials formed from petroleum resources, because they are harmless to human bodies and do not destroy natural circumstance. These products have been used for years and are safe to human bodies. They are also buried in earth and degraded with bacteria or microorganism.

Some products formed from starch have already been available, such as starch based loose bill obtained by extrusion processing technology in the presence of water, and trays or cups obtained by molding starch slurry with heat and foaming. The starch products are, however, poor in water resistance and strength characteristics, in comparison with those obtained from synthetic polymers. It is also proposed that starch is mixed with other biodegradable synthetic polymers to form into film, sheet or molded article, but the final products do not have sufficient properties as required for industrial products. It is still desired to develop starch products having sufficient physical and chemical properties equal to those obtained from petroleum bas d synthetic polymers.

There are some problems inherent to starch products as follow:

(a) Natural starch is generally composed of a mixture of amylose (polymer having a construction of linearly bonded glucoses) and amylopectin (bunch-shape polymer composed of amylose having branches). The linear amylose has good processability, film properties and molding abilities equal to synthetic plastics, but the amylopectin shows poor strength characteristics. Natural starch, however, does not have so much amylose content. For example, corn starch has amylose content of as low as about 25% and even high-amylose corn starch has an amylose content of about 70% or less.

Accordingly, it is difficult to employ natural starch as it is, in view of poor processability and moldability.

(b) Amylose can be extracted or separated from natural starch, but its process is complicated and yield by amylose is very low. The process does not have industrial cost effectiveness.

(c) Amylose present in natural starch generally has a molecular weight of as low as about ten thousand Da to hundred thousand Da and therefore is easily retrogradated and shows poor mechanical strength. Accordingly, ever if amylose is effectively extracted or separated from natural starch, the resultant amylose dose not has sufficient characteristics for substituting plastics.

(d) Amylose present in natural starch has a molecular weight distribution (Mw/Mn) of not less than 1.3 and therefore is a mixture of (i) low molecular weight amylose that easily crystallizes, (ii) high molecular weight amylose that easily dissolves in water and (iii) middle molecular weight amylose that is easily gelled. The three type amyloses impede with each other and the mixture does not exhibit enough characteristics in processability or the like.

(e) Amylose present in natural starch does not have complete linear structure, but has small amount of branched structure. Thus, the nucleation speed of natural amylose is fast and the natural amylose easily crystallizes by itself. This characteristics of natural amylose make the structure of film or sheet ununiform and significantly reduces transparency and mechanical strength.

(f) Amylose present in natural starch easily dissolves in hot water of not less than 130° C., but precipitates at a temperature of less than 130° C. (re-crystallization) to form white viscous solution because of the reasons mentioned in the above (c), (d) and (e). The molded article obtained therefrom also has an ununiform structure and shows poor processability, poor transparency and poor strength.

(g) Amylose present in natural starch does not easily dissolve in water at ambient temperature, but dissolves in specific organic solvent, such as dimethylsulfoxide and dimethylformamide. The use of natural amylose requires the process to recover the organic solvent, so that the process is not good for manufacturing because of cost effectiveness. Absence of good and useful solvent is also a serious disadvantage of natural amylose upon altering its polymeric properties by chemical modification.

(h) In order to modify the polymeric characteristics of natural starch, it is also proposed to graft-polymerize starch molecules with vinyl monomer, such as methyl acrylate, methyl methacrylate, or styrene. The modification raises cost of production, but does not enhance polymeric characteristics so much. Additionally the vinyl graft portions do not show biodegradation.

(i) It is difficult for natural amylose to control swelling by chemical crosslinking reaction.

Industrial application of natural amylose does not proceed so much because of the above mentioned reasons.

DISCLOSURE OF INVENTION

Accordingly, the present invention is to provide a biodegradable article formed from an amylose that does not have the defects of natural starch or natural amylose. The present inventors have found that the defects of natural amylose can be overcome by employing an entirely linear amylose that has a weight average molecular weight of not less than 100 kDa and has narrow molecular weight distribution, which is obtained by enzyme-synthesis using phosphorylase.

Thus, the present invention is to provide a biodegradable article formed from enzyme-synthesized amylose using phosphorylase, wherein the enzyme-synthesized amylose is composed of glucose monomers exclusively bonded by α-1,4-glucosidic linkage and has a weight average molecular weight of not less than 100 kDa. The article of the present invention is excellent in biodegradability, transparency, processability and strength characteristics.

BEST MODE FOR CARRYING OUT THE INVENTION (Enzyme-Synthesized Amylose)

Several methods for synthesizing amylose using an enzyme are art-known. For example, amylose can be obtained by the selective hydrolysis of α-1,6-linked branch linkage of amylopectine present in natural starch by using debranching enzyme, such as isoamylase or pullulanase (called starch-debranching method). This starch-debranching method, however, generates an amylose that has relatively short polymer chain, e.g. average polymerization degree of 15 to 20 and has broad molecular weight distribution. The enzyme debranching of a α-1,6-glucosidic linkage is not perfectly conducted and therefore this method does not provide entirely linear amylose.

It is also known to the art that glucose is bonded by an enzyme to synthesize amylose (called enzyme synthesizing method). As an example of the method, it is proposed that sucrose is used as substrate and is treated with amylosucrase (EC 2.4.1.4), which is called AMSU method. In AMSU method, however, since amylosucrase not only catalyzes the reaction for amylose synthesis, but also catalyzes some other reactions including hydrolysis of sucrose and the transfer reaction using sucrose or fructose as receptor, large amount of by-products, such as soluble oligosaccharide, are produced in addition to amylose. Accordingly, the yield of amylose reduces (see FEBS Letters 471, Montalk et al, pp 219 to 223 (2000)). In the ASMU method, control of polymerization degree and molecular weight distribution are also difficult. The amylose obtained in the ASMU method is water-insoluble or has low degree of polymerization. The article of Montalk et al. reports that, even if highly purified amylosucrase is employed, the resulting amylose has a molecular weight of 8,941 (i.e. polymerization degree 55). Such amylose easily precipitates and is easily retrogradated, thus showing poor mechanical strength. The enzyme-synthesized amylose by the AMSU method is not appropriate for biodegradable article that needs sufficient strength.

As an enzyme-synthesizing method other than the AMSU method, a method using phosphorylase is proposed. Phosphorylase is an enzyme that catalyzes phosphorolytic reaction. For example, amylose can be synthesized by the action of glucan phosphorylase (α-glucan phosphorylase, EC2.4.1.1.: generally called phosphorylase) to transfer glucosyl unit from glucose-1-phosphate (called as G-1-P) to malto-heptaose primer and the like (called GP method). It is also known that amylose can be synthesized by the combined activities of sucrose phosphorylase (EC 2.4.1.) and glucan phosphorylase on sucrose in the presence of inorganic phosphate (called SP-GP method). The GP method has a disadvantage that G-1-P is expensive and therefore method is costly high. It, however, has advantages that entirely linear amylose is obtained since the glucose monomers are exclusively linked each other with α-1,4-glucosidic linkages, and that polymerization degree can be freely controlled. The SP-GP method has an advantage that cheap raw material, sucrose, can be used to reduce the production cost of amylose, in addition to the advantage that entirely linear amylose with controlled degree of polymerization, similar to the GP method.

The present inventors have reached the present invention by selectively using a linear type enzyme-synthesized amylose having a weight average molecular weight of not less than 100 kDa, preferably not less than 300 kDa, more preferably not less than 600 kDa and a narrow molecular weight distribution (Mw/Mn) of not more than 1.25, preferably not more than 1.15, which is obtained by enzyme-synthesis using phosphorylase.

The enzyme-synthesized amylose employed in the present invention is one that is obtained by enzyme-synthesizing methods using phosphorylase, preferably by GP method and/or by SP-GP method. The enzyme-synthesized amylose of the present invention has desirable molecular weight range and narrow molecular weight distribution and also has entirely linear molecular structure. The amylose can provide a biodegradable article exhibiting superior characteristics to those produced from conventional starch.

The enzyme used in the enzyme-synthesizing method, such as GP method and/or SP-GP method, is phosphorylase and is not limited as long as amylose can be synthesized with desired molecular weight range and molecular weight distribution, including anyone derived from animals, plants, microorganism or the like. The enzyme may also be one produced by genetic engineering technique. Preferred is sucrose phosphorylase derived from a bacterium of Leuconostoc species. Glucan phosphorylase can preferably be one derived from plants, especially potatoes or sweet potatoes, which are more useful.

The biodegradable article of the present invention comprises enzyme-synthesized amylose having Mw of not less than 100 KDa, preferably not less than 300 kDa, more preferably not less than 600 kDa and Mw of not more than 6,000 kDa and having Mw/Mn of not more than 1.25, preferably within the range of 1.0 to 1.2, more preferably within the range of 1.0 to 1.15, which is preferably obtained by GP method or SP-GP method. The above methods can produce amylose having Mw of more than 6,000 kDa, but in view of industrial applicability of actual manufacturing, amylose having not Mn of more than 6,000 kDa is preferable.

The enzyme-synthesized amylose having Mn of not less than 600 kDa is employed and formed into coating or film, the resulting article shows high tensile strength of not less than 800 kgf.cm$^2$ (78.4 MPa). Such high tensile strength ranges are not obtained from article formed from natural starch or natural amylose and is superior to those of oriented polystyrene of 700 kgf/cm$^2$ (68.6 MPa). The high tensile strength ranges are suitable for medical seaming string or film.

The amylose having molecular weight of at least 300 kDa, preferably at least 600 kDa and narrow molecular weight distribution shows stable water solubility. The amylose having molecular weight within the range of 100 to 300 kDa shows lower viscosity than the higher molecular weight amylose, and therefore is easily handled. The lower molecular weight amylose, however, is gelled or crystallized easier than the higher molecular weight amylose and therefore it is difficult to form film or to process it into some shape. The disadvantages (gelation or crystallization) of the lower molecular weight amylose can be improved with enhancement of processability by chemically modifying the amylose, for example introducing hydrophobic groups into the amylose as explained hereinafter. The chemical modification is not always applied to the lower molecular weight amylose, but applied to the higher molecular weight amylose having Mw of not less than 300 kDa, if necessary.

(Chemical Modification of Enzyme-Synthesized Amylose)

The enzyme-synthesized amylose of the present invention can be subjected to chemical modification of esterification, etherification, oxidation, graft polymerization and/or crosslinking reaction. The modified amylose has high retrogradation stability and high processability.

The esterification can be conducted by reacting the amylose with acid anhydride, organic acid, acid halide, ketene or other esterifying agent in the presence or absence of solvent. Acylation, such as acetylation or propionation, can be done on the amylose.

The etherification can be conducted by reacting the amylose with alkyl halide or dialkyl sulfate in the presence of alkali, similar to the starch modification.

The oxidation can be generally conducted by oxidizing at low temperature in aqueous suspension or by heating powdered amylose in the presence of oxidizing agent. The oxidizing agent can preferably be sodium hypochlorite, hydrogen peroxide and the like.

The graft polymerization can be conducted either by adding vinyl monomer, such as acrylic acid or methacrylic acid to the amylose in the presence of iron or cerium ion or by condensation-polymerization to branchy add carboxylic acid having hydroxyl group, such as lactic acid to the amylose, similar to usual grafting of starch. In order to keep biodegradability as high as possible, the grafting agent should also be bidodegradable as lactic acid or caprolactone.

The crosslinking can be conducted by reacting the amylose with formaldehyde, epichlorohydrin, glutaraldehyde, diglycidyl ether and est r, similar to conventional crosslinking of starch.

In case where the groups introduced into the amylose molecule by chemical modification are hydrophobic, the higher the degree of substitution (DS), the more hydrophobic the modified amylose. Accordingly, the lower molecular weight amylose can control absorbability or biodegradability in organism and can process easily with lower viscosity. The chemical modification also alters the biocompatibility, thus the resulting article of the present invention is applicable to medical materials.

The thermoplastic properties of the amylose increase with increasing the amount of substituent groups introduced by chemical modification. The bulky groups introduced by graft reaction may often reduce the temperature of heat flowabilty significantly. The reduction of heat flowability improves molding processability in plastic molding apparatus, in comparison with the unmodified amylose.

The chemically modified amylose can be used as film, sheet or molded articles in a field requiring water resistance. The modified amylose may also be easily formed into aqueous solution, paste or cream, which is contained in glass bin or tube, and kept for long period of time.

The enzyme-synthesized amylose can be formed into gel having high water absorption by graft reaction or made into water or solvent insolubilization by crosslinking reaction. The enzyme-synthesized amylose can be formed into gel having broad swelling degree by graft polymerization or crosslinking reaction.

(Biodegradable Article)

The biodegradable article of the present invention can be produced by (a) the enzyme-synthesized amylose and/or its modified one, or a combination of the amylose or its modified one (a) and (b) another polymer material.

The other polymer material (b) is not always biodegradable. In case where the other polymer material (b) is not biodegradable, the resultant article is biodegraded with the portion of the enzyme-synthesized amylose of the present invention and remains undegraded with the other portion. The more the amount of the amylose, the more biodegradable the article. In case where the other polymer is biodegradable, the polymer (b) includes polylactate, polyglycolic acid, poly(β-hydroxybutylate), poly(β-hydroxyvalerate), poly(β-hydroxyalkanoate), aliphatic biodegradable polyester or the like. Preferred other polymer (b) is polylactate.

The biodegradation of the enzyme-synthesized amylose of the present invention is very fast in natural surroundings, and the intermediate material of the degrading process is also harmless to the human beings. An amount of the enzyme-synthesized amylose is preferably made larger. In case where the amylose is combined with the other polymer, it is preferred that an amount ratio of enzyme-synthesized amylose/other polymer is within the range of 99/1 to 1/99, preferably 95/5 to 5/95, more preferably 90/10 to 10/90.

The biodegradable article may contain plasticizer to improve processability and strength characteristics. The plasticizer for the present invention includes urea, natural oil (such as, soy bean oil, caster oil and the like), acid ester that is used in chemical field and biodegradable. The biodegradable acid ester includes mono- or di-alkyl phthalate, alkyl succinate, alkyl lactate, alkyl citrate, alkyl adipate, alkyl stearate, alkyl oleate, alkyl ricinoleate, alkyl elcate or the like. The alkyl group includes methyl, ethyl, propyl, hexyl, heptyl, octyl or the like. The acid ester can also be ester of glycerol, such as glycerin triacetate, glycerin mono-, or di-acetate, glycerin mono, di- or tri-propionate, glycerin mono-, di-butanoate, glycerin mono-, di-, or tri-stearate or the like. Preferred plasticizer is urea or glycerin for reducing flowable temperature or enhancing elongation.

The biodegradable article of the present invention may contain inorganic or organic additives for extending characteristics range of the final product. Examples of the inorganic or organic additives are inorganic additives, such as talc, titanium dioxide, calcium carbonate, clay, sand, chalk, limestone, diatomaceous earth, silicate, mica, glass, quartz and ceramics; and organic additives, such as starch, cellulose, wood powder and fiber; and the like.

(Application of the Biodegradable Article)

The biodegradable article of the present invention can be shaped into film or sheet by a conventional plastic molding apparatus. Molding is not specifically limited, but includes extrusion molding, injection molding, filming molding or the like. The article of the present invention can be formed by applying the molding composition containing the specific amylose to a conventional molding facility and apparatus.

The article has a shape of film, sheet, yarn, fabric, nonwoven fabric or the like. The article can be applied to a container for hamburgers, hot dogs, fried potatoes, ball-shape baked batter (tako-yaki), pasted rice, steamed rice, ice cream, Chinese noodle (or larmen), curried rice, vegetable, fruit, meat, fish, juice, coffee, beer, milk and the like; and an edible container, such as a corn cup for ice cream. It is also applicable to flower pots, tees for golf, packaging materials, commodities or the like.

When the biodegradable article of the present invention is applied to packaging materials, the packaging materials have superior plastic characteristics, such as transparency and glossy appearance to conventional plastic film and the content of the package can be seen with color and design through the packaging material. The biodegradable article has antistat effect and therefore does not have dust absorption on the surface during usage or storage, especially printing. When the article is in the shape of film, the film can be heat-sealed or wet-adhered.

The biodegradable article obtained from the enzyme-synthesized amylose of the present invention has good processability and good strength characteristics and therefore is applied to the field of paint or adhesive that usually employs starch or water soluble synthetic polymer, such as polyvinyl alcohol. The application includes (i) glue for fiber processing, such as yarn glue, dressing glue or printing glue; modifying agent for processing fabric with modifying resin; adhesive for felt or non-woven fabric, (ii) pigment binder or surface size agent for paper processing, (iii) adhesive for paper, such as paper bags, paper boxes, corrugated paper, paper tubes; bookbinding adhesive or desk work adhesive, (iv) remoistening adhesive for gum tapes, mail stamps, labels and the like, (v) adhesive for plywood; and the like.

It is also applied to matrix material for fertilizer or pharmaceuticals or agricultural chemicals, although the matrix material has usually been water soluble synthesized polymer, natural starch or protein.

The biodegradable article of the present invention is buried in earth and is decomposed by bacteria or microorganism. The article does not give rise to environmental pollution problem of waste and therefore is different from conventional article formed from synthetic plastics. Time for decomposition is not specifically limited and depends on composition of article or condition of surrounding, but usually is in time period of several weeks to several months. The article can be also used for feedstuff or compost other than embedding in earth, although it depends on the final shaped products.

The biodegradable article can be capsules formed from the enzyme-synthesized amylose and/or its modified one.

According to the present invention, the capsules can be applied to wide variety of fields by changing its content and their shape and form are not limited.

The capsules can be obtained by art-known methods, such as (i) a rotally method for a soft capsule wherein content is covered with two pieces of sheet and shaped in a mold, (ii) a chemical method for a soft capsule, such as curing and covering in air or liquid, and (iii) a method for a hard capsule, wherein a male capsule element and a female capsule element are combined with each other.

The capsules are applied to industrial products, pharmaceuticals or agricultural chemicals, medical products, feedstuff, fertilizer, commodities or cosmetics.

According to the present invention, the capsule shell is formed from the chemically modified amylose of the present invention and therefore can be modified in required characteristics against the content of the capsule (such as hydrophobic nature or lipophilic nature and hydrophilic nature) or required characteristic to applicable usage (such as, processability, mechanical characteristics, film forming ability and affinity with human body), by changing degree of modification (DS) or formulating additives or fillers. In case where the capsules are obtained from enzyme-synthesized amylose that is chemically modified and has low molecular weight, the resulting capsules have superior stability to retrogradation.

The content of the capsules is not limited and can be solid powder, hydrophilic or hydrophobic liquid or solution. If the content is hydrophobic, the capsules are formed from non-substituted or low acetylated hydrophilic amylose. If the content is hydrophilic, the capsules are formed from high acetylated hydrophobic amylose. In case where the capsules are orally administered, the capsules are made digestible or decomposable in the digestive organ, and in case where the capsules are applied to pharmaceutical medicines or medical products, the capsules are made decomposable or absorbable in the body.

The enzyme-synthesized amylose of the present invention is made of low molecular weight carbohydrate material, such as glucose-1-phosphate and therefore is harmless to human body because of no invasion of virus, bacteria or prion. The biodegradable article of the present invention can be applied to biocompatible medical material or medical appliance using the biocompatible medical material. By the term "medical material" is meant one that is directly applied to human body on the purpose of medical treatment. The medical appliance is one that is applied to diseased portions, such as skin, muscular tissue or internal organ tissue on the purpose of medical treatment, similar to the medical material, formed from a combination of the medical material and another substrate, solvent, part or device. The medical appliance, for example, includes adhesion inhibitor that interposes between diseased tissues and inhibits adhesion of tissue; tissue adhesive that applies on a diseased portion, such as seamed portion to adhere the tissues; wound dressing to cover the diseased portion, such as injured portion to protect; hemostatic or tampon that is applied to diseased portion, such as injured portion or dissected portion to stop brood flowing; or the like.

In the present invention, the affinity between the medical materials and human body can be controlled by changing a ratio of substitutent groups, i.e. hydrophilic group and hydrophobic group or by changing DS as chemical modification, as mentioned above. The article also has decomposition and/or absorption in vivo after finishing healing.

An amount of the medical material or medical appliance is changeable based on area of diseased portion, time and period for forming gel and the like. In this context, the term "gel formation" means gelation of the medical material absorbing or keeping body fluid or brood oozing out from diseased portion. The gelation of the medical material keeps the diseased portion wet condition and promotes formation of scar skin and prevents invasion of bacteria and the like.

According to the present invention, the medical material or medical appliance can be formed by mixing the above mentioned components (the enzyme-synthesized amylose and/or its modified one (a), other polymer material (b) and optional additives, such as plasticizer) and forming into desired shape. Sterilizing can be conducted either after mixing or after forming or the both. The medical material or medical appliance can be put into a pouring bottle (injector type container) together with propellant and sprayed out from the bottle onto diseased portion. It may also be formed into a compressing material or a sealing agent composed of a coating layer and a releasable protective sheet and then applied to a diseased portion.

The medical material or medical appliance is inherently harmless to the human body and has biocompatibility or mechanical characteristics. It can be formed into thread or fabric, non-woven fabric, film, sheet, tube, capsule or other molded article, paste, cream or a combination thereof.

The medical material or medical appliance can be applied to variety of mammals, such as domestic animals and pets, other than human beings. It is useful for health support, internal treatment and surgical treatment (or surgical operation).

EXAMPLES

Comparative Example 1

Extraction of Amylose From Potato Starch

A starch of 20 g obtained from potatoes was charged in 1 liter of hot water with stirring to form a 2% gelatinized starch solution. The solution was put in an autoclave at 120° C. for 30 minutes and filtered with glass filter to remove an indissolved portion. To the filtrate, butanol was added in an amount to form a 15% butanol-saturated solution and heated to 95° C. for 30 minutes, followed by slowly cooling in a vacuum bottle. After one day, the precipitated material was centrifugally separated to obtain a mixture of amylose and butanol. The butanol saturated solution was precipitated again and to separate a complex of amylose and butanol. The separated complex was rinsed two times and vacuum dried. The resulting amylose was 3.5 g and had a weight average molecular weight Mw of 450 kDa and a molecular weight distribution (Mw/Mn) of 1.9. The resulting amylose did not dissolve in cool water and, even if it was put into an autoclave at a temperature of 130° C., the solution was still white milky solution. The solution was formed into a film by a cast method, but the film could not be obtained because of its brittle properties. No strength determination could be conducted to the film.

Comparative Example 2

Extraction of Amylose From Corn Starch

An amylose having a molecular weigh of 250 kDa and a molecular weight distribution of 1.4 was obtained as generally described in Comparative Example 1, with the exception that corn starch was employed instead of potato starch. The resulting amylose had similar appearance and poor strength characteristics to one of Comparative Example 1. The resulting film was brittle and could not be subjected to strength determination.

Example 1

Synthesis of Enzyme-Synthesized Amylose (DS:0.0)

Sixty gram of Glucose-1-phosphate (G-1-P) and 5 mg of maltopentaose were dissolved in 1.3 liter of 0.2 M maleic acid buffer solution (pH 6.0), to which 1,500 unit of phosphorylase derived from potatoes was added. It was then mixed at 50° C. to react. After reacting 86 hours, the solution was heated to inactivate the enzyme and filtered with glass filter to remove the inactivated enzyme. To the filtrate, two times volume amount of ethanol was added to precipitate the amylose and centrifugally separated. The precipitate was rinsed two times with 300 mili-little of a mixture of water and ethanol (1:1) to remove the co-present G-1-P. It was then rinsed two times with ethanol and vacuum dried at 70° C. The resulting amylose was 18.7 g. One unit of phosphorylase is an amount that 1 μmol of phosphoric acid is produced in one minute. The resulting enzyme-synthesized amylose had a Mw 820 kDa and a Mw/Mn of 1.05.

The film produced from the resulting amylose was subjected to determination of light absorbance to the light of wave length of 300 to 800 nm. The absorbance value for the amylose film was as high as not more than 0.05, although the absorbance for a film produced from natural amylose was high as 0.18 to 0.38. The enzyme synthesized amylose was dissolved with at least 2 g in 100 mili-little of water at 15° C. and with at least 5 g in 100 mili-little of water at 70° C. It was not crystallized at room temperature and therefore did not form white milky turbidity.

A solution of the enzyme synthesized amylose was casted on a polystyrene plate and dried at 37° C. for one hour and then at 40° C. for 24 hours to form a film. The film had excellent transparency and had a tensile strength of not less than 500 Kgf/cm$^2$ (490 MPa) that equaled to those of polyethylene or polypropylene. The amylose that had been adjusted to equilibrium moisture indicated thermoplastic properties and was easily molded into film or sheet by heat pressing. The amylose was mixed with plasticizer (e.g. glycerin or urea) and was solution-extruded to easily form a sheet.

In conventional technique, natural starch or glue has been used as paper adhesive for paper bags, paper boxes, corrugated paper, paper tubes or book adhesive, but these natural adhesive has had problems such as quality difference or modification during storage. In case where the amylose of the present invention was applied to adhesive for paper, an aqueous solution with solid content of 10% was coated with paper with 10 g/cm$^2$ to show a strength of 10 Kg/cm$^2$ that was several times higher than that (4 Kg/cm$^2$) of gelatinized corn starch solution.

Example 2

Synthesis of Enzyme-Synthesized Amylose

An amylose having Mw 1,400 kDa was obtained with reaction time of 75 hours as generally described in Example 1, with the exception that an amount of G-1-P was increased to 100 g and an amount of maltopentaose was reduced to 2.5 mg. The resulting amylose had Mw/Mn of 1.07 and an yield of 17 g.

This experiment proved that a change of a weight ratio of G-1-P and maltopentaose could control molecular weight of the amylose. The extension of reaction time made it possible to obtain high molecular weight amylose.

Example 3

Synthesis of Enzyme Synthesized Amylose

This example compares characteristics of the enzyme synthesized amylose of the present invention with those of the amylose obtained by art-known AMSU method.

Each one litter reaction vessel was charged with 6 mM phosphoric acid buffer solution (pH 7.0), 106 mM sucrose and malto oligosaccharide having each different concentration (2,200 mg/litter, 880 mg/litter, 176 mg/litter, 132 mg/litter, 44 mg/litter or 8.8 mg/litter), to which 1 unit/mili-little of purified glucan phosphorylase derived from potatoes and 1 unit/mili-little of sucrose phosphorylase derived from Leuconostoc mesentroides were added and kept at 37° C. for 16 hours to terminate reaction, thus obtaining amylose. Yield (%), weight average molecular weight (Mw) and molecular weight distribution (Mw/Mn) of the resulting amylose were determined and the results show in the following Table 1.

TABLE 1

| Sample No. | Concentration (mg/litter) of malto oligosaccharide mixture | Yield (%) | Mw (kDa) | Mw/Mn | Appearance of amylose |
|---|---|---|---|---|---|
| 1 | 2,200 | 95.1 | 11.9 | 1.05 | Precipitation |
| 2 | 880 | 90.4 | 29.8 | 1.03 | Precipitation |
| 3 | 176 | 90.7 | 84.4 | 1.02 | White turbid solution |
| 4 | 132 | 88.8 | 110.0 | 1.01 | Transparent solution |
| 5 | 44 | 87.9 | 276.1 | 1.01 | Transparent solution |
| 6 | 8.8 | 85.3 | 741.9 | 1.01 | Transparent solution |
| Amylose of AMSU Method | 0 | 57.0 | 8.9 | 1.1 | Precipitation |

In Table 1, values of amylose obtained by AMSU method, as described in FEBS Letters 471, Montalk et al., pp 219-223, (2000), are also shown, in order for comparison.

As is apparent from Table 1, change of concentration ratio of sucrose and primer (i.e. malto oligosaccharide mixture) provides change of molecular weight of amylose within the range of Mw 11.9 to 741.9 kDa. The amyloses thus obtained had narrow weight molecular distribution of not more than 1.05. Samples 1 and 2 formed precipitation of low molecular weight amylose, but the precipitation did not occur as degree of polymerization increases. Samples 4 and 5 kept transparent and therefore water soluble amylose was obtained.

The enzyme synthesized amylose of the AMSU method for comparison was water insoluble amylose having a molecular weight of 8.9 kDa, although the reaction was carried out under the condition where high molecular weight amylose was expected to be produced.

As is apparent from the above experiment, the SP-GP method used in the present invention can produce water soluble amylose having high molecular weight and narrow molecular weight distribution, which has not obtained by the art-known AMSU method.

Example 4

Crosslinking Reaction of Enzyme-Synthesized Amylose

Thirty two gram of 2.5% aqueous solution of the amylose obtained in Example 1 was adjusted to pH 12.8 with sodium hydroxide solution and reacted with 0 to 3.840 g of nonaethylene glycol diglycidyl ether (Denacol EX-830 having molecular weight of 526.6, available from Nagase Sangyou K.K.). The resulting solution was casted over a polyethylene panel at 37° C. for one hour and then at 40° C. for 24 hours to obtain a film of the enzyme synthesized amylose gel. The film was rinsed with pure water to remove remaining Denacol EX-830, sodium hydroxide and non-crosslinked amylose.

The film using an amount range of 0 to 0.0245 g of Denacol EX-830 was swelled at room temperature and heated to 130° C. to melt. However, the film using an amount range of 0.483 to 3.840 g of Denacol EX-830 was swelled but did not melt at heated temperature.

The films obtained above were all transparent and showed excellent strength characteristics.

Comparative Example 3

Crosslinking Reaction of Amylose Extracted From Corn Starch

Crosslinking reaction was conducted as generally described in Example 4, with the exception that the amylose of Comparative Example 2 was employed. The casted films were all opaque and brittle.

Comparative Example 4

Film formation was conducted as generally described in Example 4, with the exception that the amylose (Mw 29.8 kDa and Mw/Mn 1.03) of Sample 2 obtained in Example 3 was employed. The resulting films were too brittle to determine strength properties.

Example 5

Film formation was conducted as generally described in Example 4, with the exception that the amylose (Mw 110 kDa and Mw/Mn 1.01) of Sample 4 obtained in Example 3 was employed. The resulting film had a tensile strength of 430 Kgf/cm$^2$ (42.14 MPa).

Example 6

Ten gram of the amylose obtained in Example 1 was dissolved in 80 g of dimethylsulfoxide and mixed with 2 g of sodium carbonate, to which 16 g of vinyl acetate was added and reacted at 80° C. for 120 minutes. After reaction, water was added thereto to precipitate the product which was filtered and rinsed several time with water to obtain an acetylated amylose having an yield of 90%, a degree of substitution (DS) of 2.1 and a heat flowing temperature of 275° C.

Example 7

Graft Polymer of Acetylated Amylose and Its Application

Ten gram of the acetylated amylose obtained in Example 6 was charged with 60 g of ε-caprolactone and graft-polymerized at 120° C. in the presence of tin (II) octylate. The graft-polymerization proceeded as time and the reaction was terminated after about 10 minutes, which was determined with mole substitution degree (mole number of bonded ε-caprolactone per one unit of glucose) and weight increase ratio of product. The heat flowing temperature of the product reduced from 275° C. to 55° C. Graft degree was about 70 to 200% when determined by weight increase ratio. The resulting film was excellent transparency and was non-crystallinity because of no heat absorption peak when determined by a differential scanning calorimeter (DSC).

The acetylated amylose having a graft degree of 61.5% was formed into a heat-pressed sheet having 25 μm. It was then cut into a test sample having width 1 cm and length 5 cm and subjected to test of tensile strength by Tensilon at a tensile speed of 50 mm/minute. The sample had a tensile strength of 180 Kgf/cm$^2$ (17.64 MPa) and an elongation of 5%. The acetylated amylose having a graft degree of 276% was treated as described above and tested. The test sample had a tensile strength of 130 Kgf/cm$^2$ (12.74 MPa) and an elongation of 18%. Both samples showed good strength characteristics equal to conventional polyolefin.

The article, such as film or sheet, could be easily molded using plastic molding apparatus commercially available.

Example 8

Preparation of Film From Acetylated Enzyme-Synthesized Amylose

The acetylated enzyme-synthesized amylose of Example 6 and equimolar amount of poly-ε-caprolactone were mixed in a solution of acetone and methylene chloride, and then casted on a glass plate. It was remained one day and then vacuum-dried at room temperature for one hour. The resulting film was transparent and soft, which indicated good compatibility to the both polymers. The film had a tensile strength of 150 Kgf/Cm2 (14.7 MPa) and an elongation of 20%.

Example 9

Biodegradation of Amylose Film

The film obtained in Example 1 was buried in earth and completely decomposed for one week.

Example 10 (Spinning of Enzyme-Synthesized Amylose)

A 5% aqueous solution of the amylose of Example 1 was put into an extruder having a single spinning nozzle of 0.1 mm diameter and extruded into methanol at room temperature to form a filament of about 20 μm. The filament was rolled up with a bobbin and dried at room temperature. The filament, after drying, had a strength of 1,450 Kgf/cm$^2$ (142.1 MPa) and an elongation of 20%.

Example 11 (Laminate of Polylactic Acid Film Using Acetylated Amylose (DS 0.27))

An acetylated amylose having a substitution degree (DS) of 0.27 was prepared as generally described in Example 6, with the exception that 0.26 g of sodium carbonate and 2 g of vinyl acetate were employed. Five % aqueous solution of the acetylated amylose was applied with an applicator on a polylactate film having 25 μm and was dried to form an amylose film having 3 μm. Wet machine-made paper was covered on the amylose film surface of the laminate film and dried with pressing to form a three layer laminate film of paper, amylose film and polylactate film, the amylose film being functioned as adhesive.

The resultant three layer laminate was subjected to a 90 degree peeling test and the results showed excellent adhesive strength in amylose layer and interface either between paper and amylose or between polylactate film and amylose, although some destruction appeared in paper layer.

The present invention have made it possible to laminate polylactate film with biodegradable material.

Example 12

Biocompatibility of Acetylated Enzyme Synthesized Amylose

Wistar/ST male rats with 5 weeks old were fed for another one week and was checked healthy. After shaving operating portions on shoulders and buttocks, tiny pores were formed therein and pieces of filament were put in the pores. After two weeks from the operation, the rats were anatomized to pathologically observe the portions in which the filament was put in about whether inflammation reaction occurred. No inflammation was observed, thus showing good biocompatibility.

Example 13

Effect of Adhesion Inhibitor and Decomposition in the Body

The casted film obtained from the crosslinked amylose using 3.840 g of Denacol EX-830 in Example 4 was subjected to determination of effectiveness of adhesion inhibitor and decomposition in the body.

A uterine tube of a female rat was cut and sewed and the cut portion was covered with casted amylose film fertilized with ultraviolet light. The other uterine tube of the same rat was cut and sewed, and kept as it was. After one week, the control cut portion without the amylose film cured, but adhered to peritoneum. The amylose film covered portion did not have any adhesion and also decomposed completely, after the cut cured.

Example 14

Capsules Formed From Enzyme-Synthesized Amylose

Capsules were obtained by the following ingredients and process, using the enzyme-synthesized amylose (Mw 829 kDa and Mw/Mn 1.05) obtained in Example 1.

| Capsule ingredient | Amount (% by weight) |
| --- | --- |
| Shell ingredients | |
| Enzyme-synthesized amylose | 5 |
| Urea | 2 |
| Ion exchanged water | 93 |
| Content ingredients | |
| Lemon oil | 8.5 |
| Peppermint | 1.5 |
| Coconut oil | 90 |

Figure 1:
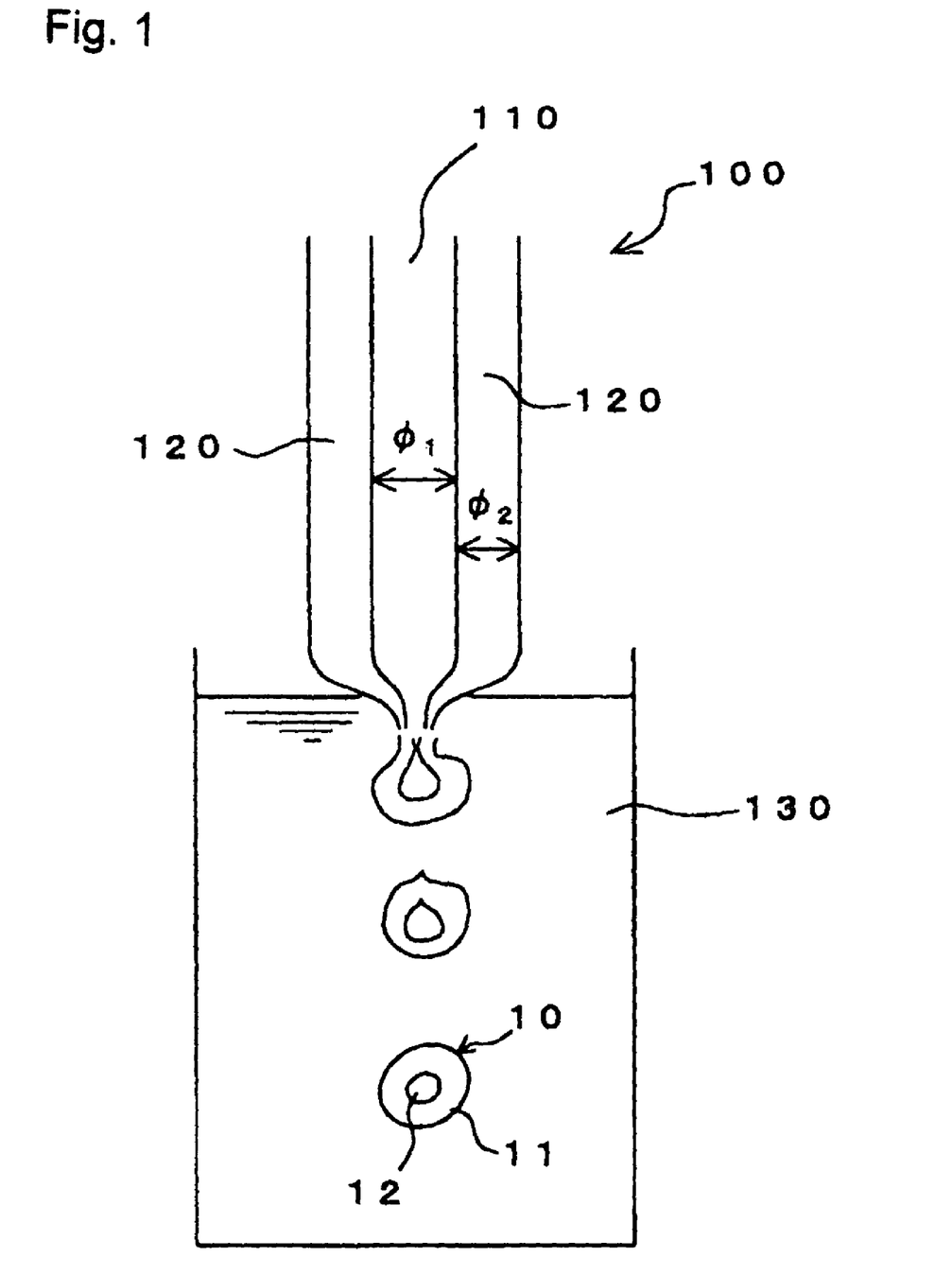
FIG. 1 schematically shows a cross-sectional view of an apparatus 100 used for producing the capsule agent 10 of the present invention by way of an art-known double nozzle liquid dropping method. In the apparatus 100, a content 12 and a capsule shell 11 are poured out respectively from a nozzle 110 having an inner diameter of $\phi_1$ and a nozzle 120 for the capsule shell having an inner diameter of $\phi_2$, and then dropped down in a mixture 130 of water and ethanol, followed by drying.

Capsules were obtained by conventional double nozzle liquid drop methods. The capsule 10 is composed of a double layer structure of a shell 11 and a content contained therein. FIG. 1 shows a sectional view of an apparatus 100 which is used for the double nozzle liquid drop method. In the method, the capsule agent poured out from the double nozzle was dropped in a water-methanol mixture 130 for drying. In the apparatus, the inner nozzle 110 for the content had a diameter ($\phi_1$) of 1.0 mm and the outer nozzle 120 of the shell had a diameter ($\phi_2$) of 1.2 mm. The resultant capsule 10 had an average diameter (d) of 1.2 mm and a covering rate was 10% by weight. The covering rate is an amount of shell based on a total weight of the capsule. The capsule 10 indicated excellent strength and good retention of content.

Example 15

Capsule of Acetylated Enzyme-Synthesized Amylose (DS:2.6)

An acetylated enzyme-synthesized amylose (DS 2.6) was obtained as generally described in Example 6, with the exception that 2.5 g of sodium carbonate and 20 g of vinyl acetate were employed. Capsules were obtained by the following ingredients and process.

| Capsule ingredient | Amount (% by weight) |
|---|---|
| Shell ingredients | |
| Acetylated enzyme-synthesized amylose (DS:2.6) | 5 |
| Diethyl phthalate | 5 |
| Acetonitrile | 90 |
| Content ingredients | |
| Acetoaminophen | 0.02 |
| Ion-exchanged water | 99.98 |

Double layer capsules were obtained as generally described in Example 14, using the above ingredients. The resulting capsules 10 had an average diameter of 1.2 mm and its covering rate was 10% by weight. The capsule 10 indicated excellent strength and good retention of content.

The invention claimed is:

1. A biodegradable article formed from enzyme-synthesized amylose using phosphorylase, wherein the enzyme-synthesized amylose is composed of glucose monomers exclusively bonded by α-1,4-glucosidic linkage, the enzyme-synthesized amylose is entirely linear amylose, the enzyme-synthesized amylose does not include cyclic amylose, the enzyme-synthesized amylose has a weight average molecular weight of not less than 100 kDa, and the enzyme-synthesized amylose has a molecular weight distribution (Mw/Mn) of not more than 1.25.

2. The biodegradable article according to claim 1 wherein the enzyme-synthesized amylose has a weight average molecular weight of not less than 600 kDa.

3. The biodegradable article according to claim 1, wherein the enzyme-synthesized amylose is chemically modified by esterification, etherification, oxidation, graft-polymerization and/or crosslinking reaction.

4. The biodegradable article according to claim 1, wherein the enzyme-synthesized amylose is enzyme-synthesized using sucrose as substrate and malto oligosaccharide as primer by the action of two enzymes of sucrose phosphorylase and glucan phosphorylase in the presence of inorganic phosphoric acid.

5. The biodegradable article according to claim 4, wherein sucrose phosphorylase is derived from a bacterium of Leuconostoc species.

6. The biodegradable article according to claim 4, wherein glucan phosphorylase is derived from plant.

7. The biodegradable article according to claim 4, wherein glucan phosphorylase is derived from potatoes or sweet potatoes.

8. A biodegradable article obtained from raw materials comprising:
   (a) enzyme-synthesized amylose using phosphorylase, wherein the enzyme-synthesized amylose is composed of glucose monomers exclusively bonded by α-1,4-glucosidic linkage, the enzyme-synthesized amylose is entirely linear amylose, the enzyme-synthesized amylose does not include cyclic amylose, and the enzyme-synthesized amylose has a weight average molecular weight of not less than 100 kDa, and/or one obtained by esterification, etherification, oxidation, graft reaction and/or crosslinking reaction thereof, and
   wherein the enzyme-synthesized amylose has a molecular weight distribution (Mw/Mn) of not more than 1.25, and
   (b) another polymer material.

9. The biodegradable article according to claim 8, wherein the other polymer material is polylactate.

10. The biodegradable article according to claim 1, wherein the article is film, sheet, string, fiber, non-woven fabric or another molded article.

11. The biodegradable article according to claim 2, wherein the enzyme-synthesized amylose is chemically modified by esterification, etherification, oxidation, graft-polymerization and/or crosslinking reaction.

12. The biodegradable article according to claim 8, wherein the article is film, sheet, string, fiber, non-woven fabric or another molded article.

* * * * *